United States Patent [19]

Haggerty et al.

[11] Patent Number: 5,420,682

[45] Date of Patent: May 30, 1995

[54] METHOD AND APPARATUS FOR COMPENSATING SPECTRAL DATA WITH A COLOR SENSOR

[75] Inventors: Alan L. Haggerty, Corcoran; Saad J. Bedros, West St. Paul, both of Minn.

[73] Assignee: Honeywell Inc., Minneapolis, Minn.

[21] Appl. No.: 87,544

[22] Filed: Jul. 2, 1993

[51] Int. Cl.⁶ .................................................. G01J 3/28
[52] U.S. Cl. ...................................... 356/328; 762/263
[58] Field of Search ............... 162/198, 258, 263, 238, 162/49; 356/326, 328

[56] References Cited

U.S. PATENT DOCUMENTS

| | | |
|---|---|---|
| 3,962,581 | 6/1976 | Zimmerman . |
| 3,965,356 | 6/1976 | Howarth . |
| 3,968,006 | 7/1976 | Zimmerman . |
| 3,994,602 | 11/1976 | Howarth . |
| 4,040,743 | 8/1977 | Villaume et al. . |
| 4,171,916 | 10/1979 | Simms et al. . |
| 4,507,556 | 3/1985 | Brenholdt . |
| 4,766,551 | 8/1988 | Begley ........................... 364/498 |
| 4,838,692 | 6/1989 | Brenholdt . |
| 5,023,804 | 6/1991 | Hoult ............................ 364/498 |
| 5,042,948 | 8/1991 | Fletcher ........................ 356/328 |
| 5,044,753 | 9/1991 | Fletcher . |
| 5,082,370 | 1/1992 | Fletcher ........................ 356/328 |
| 5,115,811 | 5/1992 | Hartlaub et al. . |
| 5,157,465 | 10/1992 | Kronberg ....................... 356/405 |
| 5,243,546 | 9/1993 | Maggard ....................... 364/571.02 |

FOREIGN PATENT DOCUMENTS 1199813  1/1986  Canada .

OTHER PUBLICATIONS

Taina Sopenlehto-Pehkonen, "Mechanical Pulp Bleaching Control Based on In-Line Brightness and Residual Measurements", from the Canadian Pulp and Paper Association 1988 Annual Meeting.

*Primary Examiner*—F. L. Evans
*Attorney, Agent, or Firm*—Paul H. McDowall; Kenneth J. Johnson

[57] ABSTRACT

A method and apparatus for interpreting spectral data in an optical sensor for a variety of uses, such as the manufacture of paper. A probe is inserted into paper pulp during the manufacturing process. The probe emits light into the pulp which is then reflected back and received. This reflected light is segmented into N different wavelengths over the visible spectrum. An N signal array is created which is used in a mathematical model to accurately depict a brightness and consistency of the paper pulp.

9 Claims, 13 Drawing Sheets

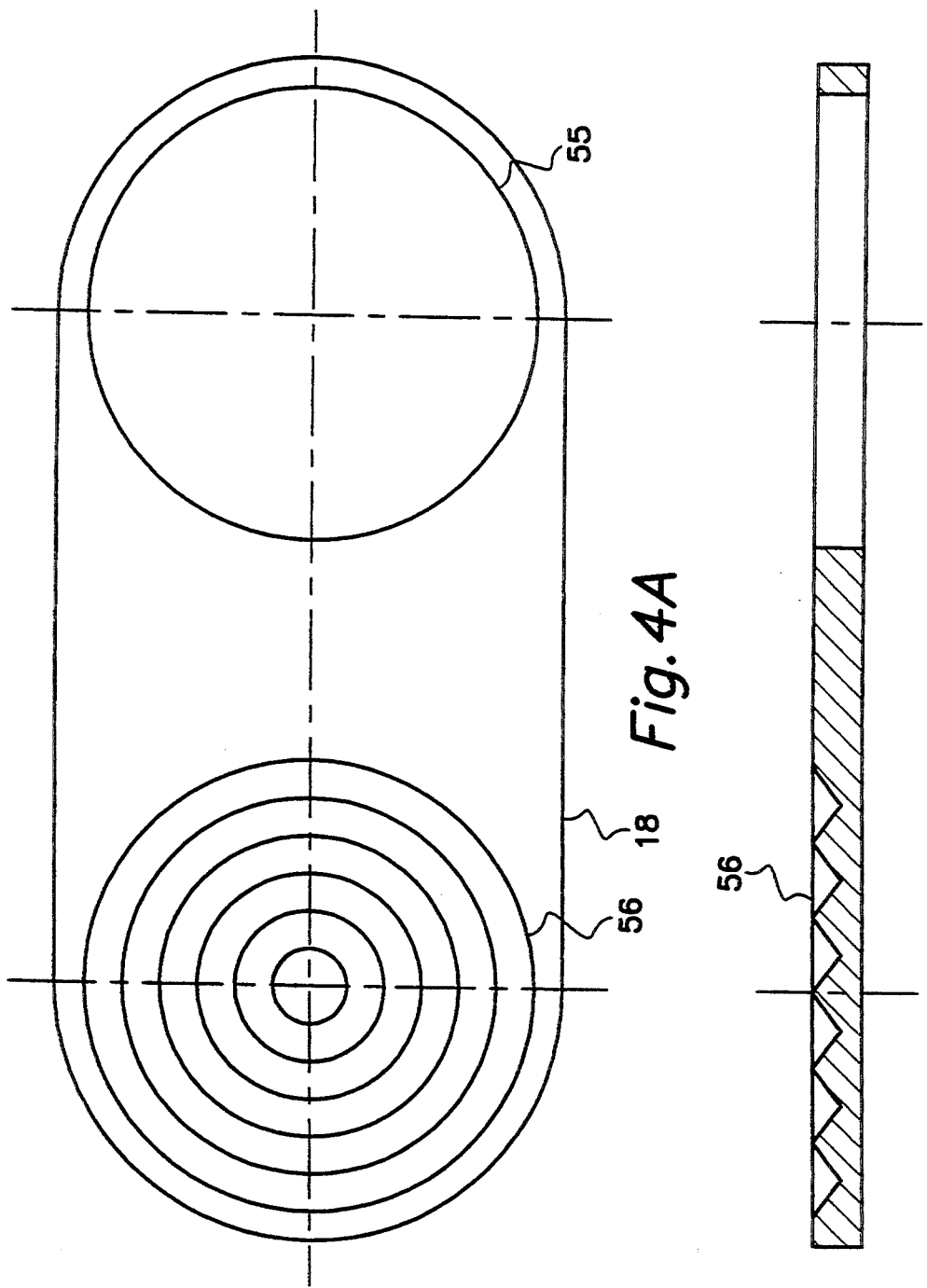

METHOD AND APPARATUS FOR COMPENSATING SPECTRAL DATA WITH A COLOR SENSOR

This application is related to copending application Ser. No. 08/087,565, filed on even day herewith and assigned to the same assignee as the instant application.

FIELD OF THE INVENTION

This invention relates to optical sensors and more specifically to interpreting spectral data in an optical sensor.

BACKGROUND

Optical sensors are used in a variety of industrial applications. One such application is the production of paper. In the production of paper, several measurements are required during the manufacturing process to ensure consistent quality of the final product. Two such measurements are consistency and brightness of the paper slurry.

During the manufacture of paper, wood fibers are separated from bulk wood by either mechanical or chemical means, or a combination. Water is mixed with wood fibers to form a wood pulp slurry. In order to achieve some measure of quality control during the process, it is essential to know the ratio of wood fibers to total mass (consistency) at every step in the process.

Some sensors used in the industry to measure consistency are mechanical in nature. One early method required a calibrated tapered rod about six inches long which was dropped from a vertical position extended a distance above the pulp. A reading was then taken of the depth to which the rod sunk in the pulp. Other mechanical sensors, by one means or another, measure the force which moving slurry produces on a mechanical arm, plate, or the like. Some limitations of these mechanical sensors are distortion due to velocity of the slurry, different wood species and drainage. Also, such mechanical systems cannot be readily installed in a tower or chamber through which pulp slurry is moving slowly, or in which pulp slurry is contained. Finally, accuracy of mechanical sensors is limited for certain pulp consistencies.

The quality of paper is also dependent on the brightness of the pulp. The final color of the paper can be predicted by using a measurement of the brightness of the pulp. Traditionally, instruments generally available and used for such brightness measurements are performed on an off-line basis. In this type of instrument, a sample is periodically taken from the pulp washer, dried, and its brightness determined from a reflectance meter. This determination can take 20 to 30 minutes.

Most modern methods of determining consistency and brightness of the pulp employ some means which emit radiant energy in the direction of the pulp. The magnitude of the energy which either passes through the pulp or is reflected back from the pulp is indicative of its brightness and consistency. This reflected energy can either be measured or compared to the magnitude of the energy emitted to determine the consistency and brightness of the pulp. The magnitude of the reflective energy can be separated into components for both consistency and brightness.

In an example of an on-line system, two sensors are positioned in the pulp to measure brightness of the pulp entering and leaving a bleaching stage. The two sensors measure the intensity of back scattered light and then compare results. The differential signal is used to control bleaching chemicals in order to optimize brightness of the pulp.

An important step in determining brightness and consistency of pulp is converting the intensity of the reflected or back scattered light into a useful measurement. One drawback of prior art systems is that the intensity of the reflected or back scattered light is measured only over a limited wavelength band. This limits the accuracy the sensor by eliminating significant amounts of data. Another drawback of prior art systems are inaccurate data models. In order to generate meaningful brightness and consistency measurements, mathematical models must be generated which accurately depict the behavior of the sensor over a particular range. With mathematical models, it is important that they are first accurate, and that their accuracy span a large range of measurements.

SUMMARY

The invention herein is a method and apparatus for interpreting spectral data in an optical sensor. The spectral data is interpreted by first illuminating an object or substance with light and then receiving the light which is reflected back. In response to the reflected light, a signal array is generated where each signal within the array is proportional to the magnitude of a particular band of wavelengths of light over a predetermined range of wavelength bands to which the sensor responds. A mathematical model is applied to the array. The mathematical model converts the magnitudes of the reflected light over the predetermined range to usable measurements of particular characteristics of the object or substance. Signals are then generated which are proportional to characteristics of the object or substance which is being measured.

The apparatus is comprised of a light source, a receiver, a light sensor, and a processor. The light sensor generates a signal array in response to the intensity of the reflected light received. The signal array is representative of the intensity of a plurality of wavelengths of light over a predetermined wavelength range. A processor applies the mathematical model to the signal array and outputs a signal whose magnitude is representative of the intensity of the reflected light over the plurality of wavelengths.

BRIEF DESCRIPTION OF THE DRAWINGS

FIG. 4a is a top view of the near reflector and FIG. 4b is cross sectional view of the near reflector.

DESCRIPTION OF THE PREFERRED EMBODIMENT

Figure 1:
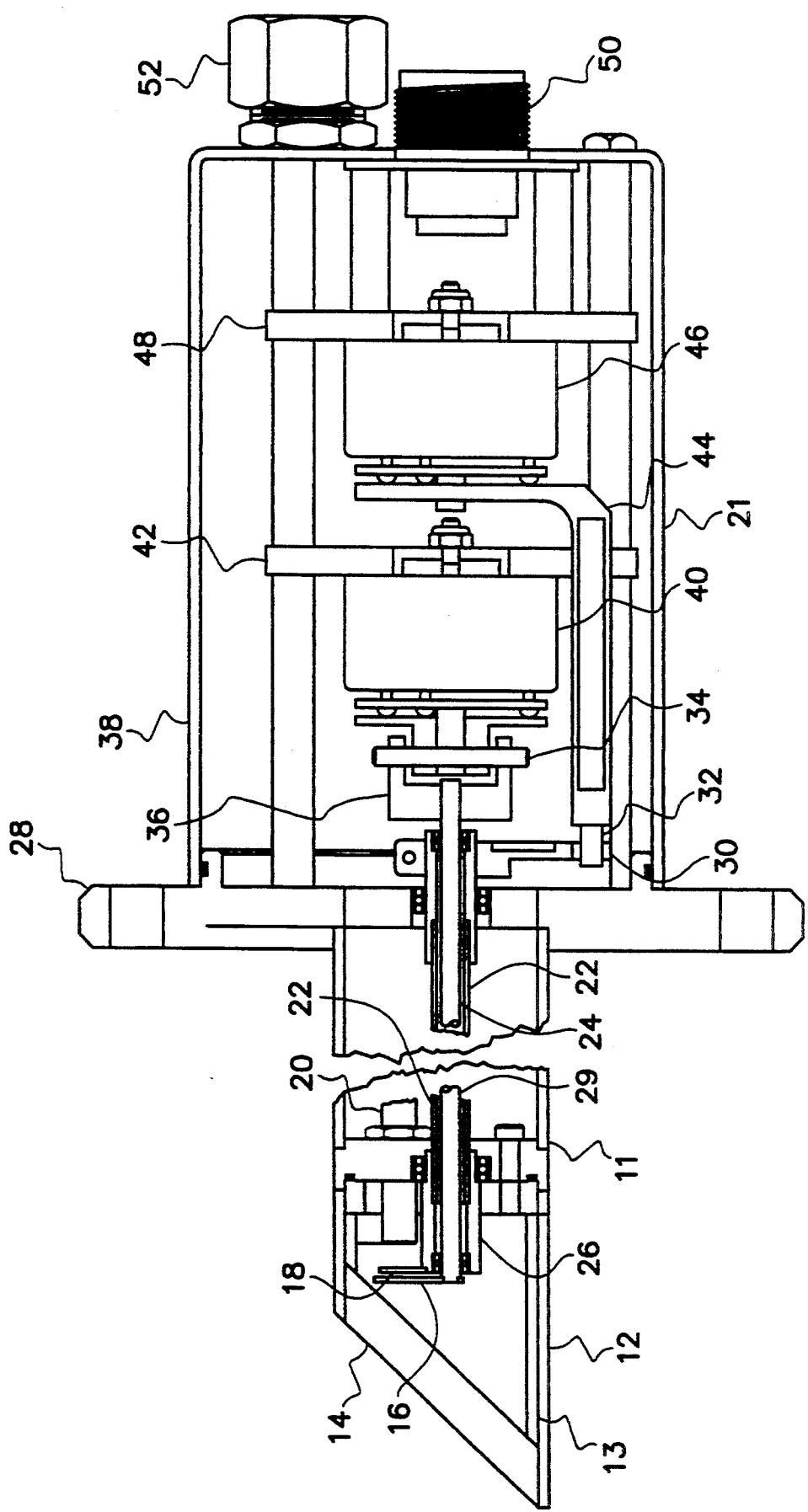
FIG. 1 is a cut-away view of the consistency and brightness sensor.

Disclosed in FIG. 1 is a preferred embodiment of sensor assembly 10. The major components of sensor assembly 10 are probe 11 and motor assembly 21. The probe 11 has a probe enclosure 12 with a window 14. Window 14 is made of a transparent material and is set at an angle to reduce reflectivity effects and improve flow characteristics over the probe. Within the enclosure is fiber-optic bundle 20 which has two functions. The bundle emits light which passes through the window 14, and then receives light which is reflected back. Also mounted within the probe enclosure are far target 16 and near target 18. The far target 16 is mounted on drive shaft 24 which passes from the probe to motor assembly 21. The near target 18 is mounted on adapter 26. The adapter 26 is mounted on the tube drive shaft 22 which encloses shaft 24. The tube drive shaft runs into the motor assembly 21. The tube shaft and drive shaft allow the targets 16 and 18 to rotate independent of each other. The targets are mounted so that they both rotate in front of the fiber-optic bundle 20.

Within the motor assembly 21, the drive shaft 24 is attached to outer coupling drive 36. The coupling drive 36 is connected to far target solenoid 40. The solenoid provides torque to rotate the far target. The tube drive shaft 22 is connected to near target arm 30. The near target arm is connected to near target solenoid arm 44 which in turn is connected to near target solenoid 46. Near target solenoid 46 provides torque to rotate near target 18. The solenoids 40 and 46 are mounted within the motor housing 38 by solenoids mounts 42 and 48, respectively. Power is provided to the solenoids through solenoid drive power connector 50. The fiber-optic bundles pass out of the motor housing through the fiber-optic strain relief 52. The sensor is mounted on a pulp container by use of the installation bracket 28.

Figure 2:
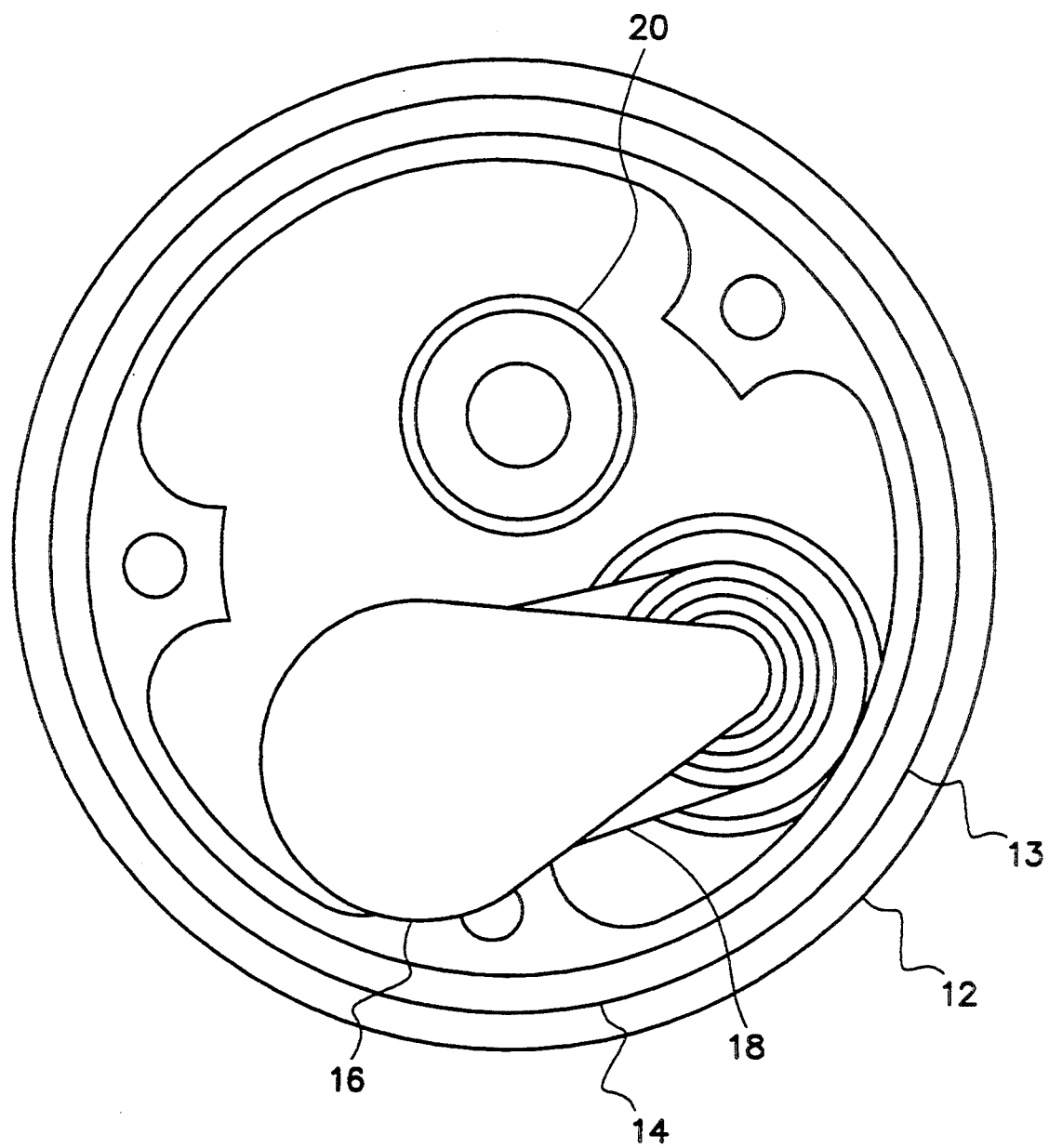
FIG. 2 is a front view of the probe, through the probe enclosure window.

FIG. 2 is an end view of the probe looking back through the window 14. As can be seen, targets 16 and 18 mounted so as to rotate up in front of the fiber-optic bundle 20 and then back again. Shown is the position of the targets when the probe is in its operational mode.

Figure 3A:
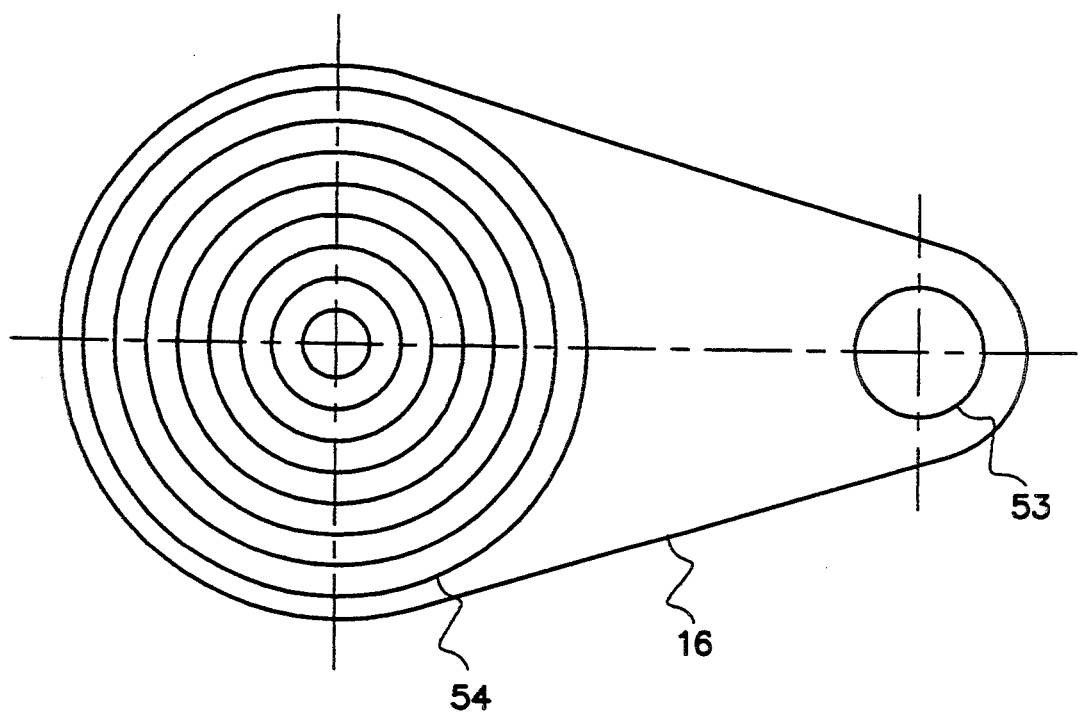
FIG. 3a is a top view of the far reflector and FIG. 3b is a cross sectional view of the far reflector.
Figure 3B:
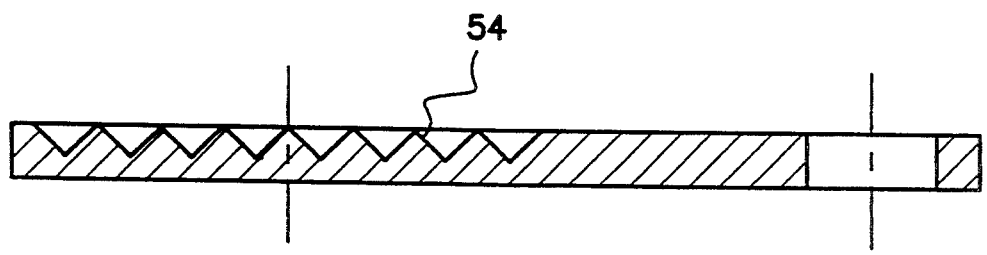

Shown in FIGS. 3a and 4a are top views of far target 16 and near target 18, respectively. On one end of the far target 16 is reflective area 54 and on the opposite end mounting hole 53 for mounting the target on the drive shaft 24. Near target 18 has reflective area 56 and mounting hole 55 for mounting on adapter 26. Each of the reflective areas 54 and 56 is of a known and different reflectivity. FIGS. 3b and 4b show a cross sectional view of the targets. The reflective areas 54 and 56 have a serrated shape to minimize mirror like reflections back to the fiber optic bundle. The serrated edges reradiate light in a diffuse manner to better indicate the actual reflectivity of the target.

This embodiment is most especially adapted to be used for pulp in paper making. Where used for objects or other work substances, those of ordinary skill in the art can easily modify the structure to better reflect these operating conditions without going outside the scope of the claims of this invention.

Figure 5:
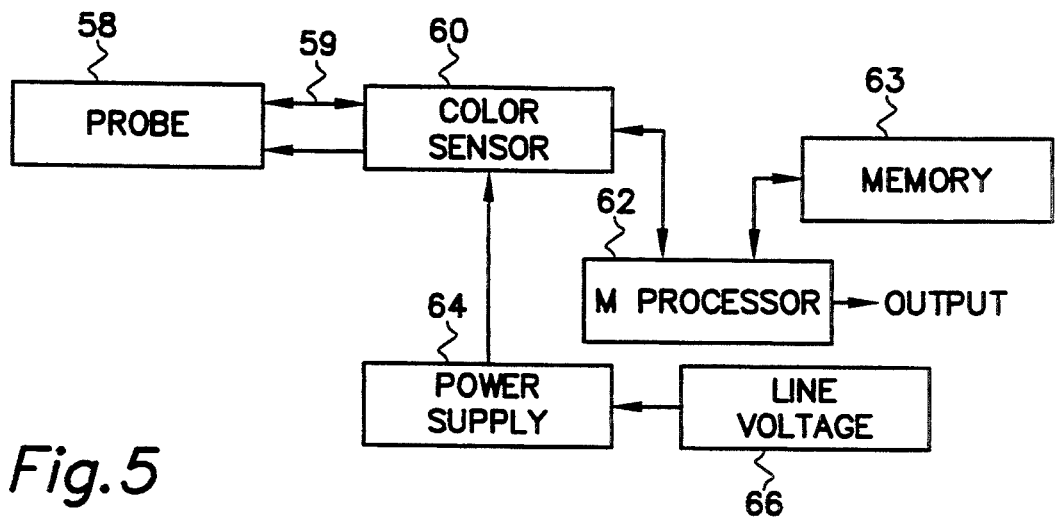
FIG. 5 is a block diagram of the brightness and consistency sensor.

Shown in FIG. 5 is a block diagram for components of the optical sensor. The probe 58, which is inserted into the pulp stream, radiates light. Some of the light is absorbed by the paper pulp and some reflected (thus it is re-radiated) with a high correlation to pulp consistency and brightness. The reflected light is collected by the probe and transmitted by fiber-optic cable 59 back to color sensor 60. The color sensor in this embodiment is a model manufactured by the Microswitch Company of Freeport, Ill. The color sensor generates a $128 \times 1$ color spectrum over the visible light wavelength range (400 to 800 NM). Although the visible light range is used in this preferred embodiment, it is possible that other wavelength ranges which extend over other domains in the electromagnetic spectrum, such as ultraviolet and infrared, could be used. The color spectrum is transmitted by electronic signal to the microprocessor 62. The microprocessor is connected to memory/software 63. Power for the optical sensor is provided by line voltage 66 through power supply 64.

In an alternate embodiment of the invention, the targets are rotated manually, rather than through use of solenoids. This would provide a lower cost sensor and avoid any reliability problems due to the operation of electric motors in a hostile environment.

Figure 6:
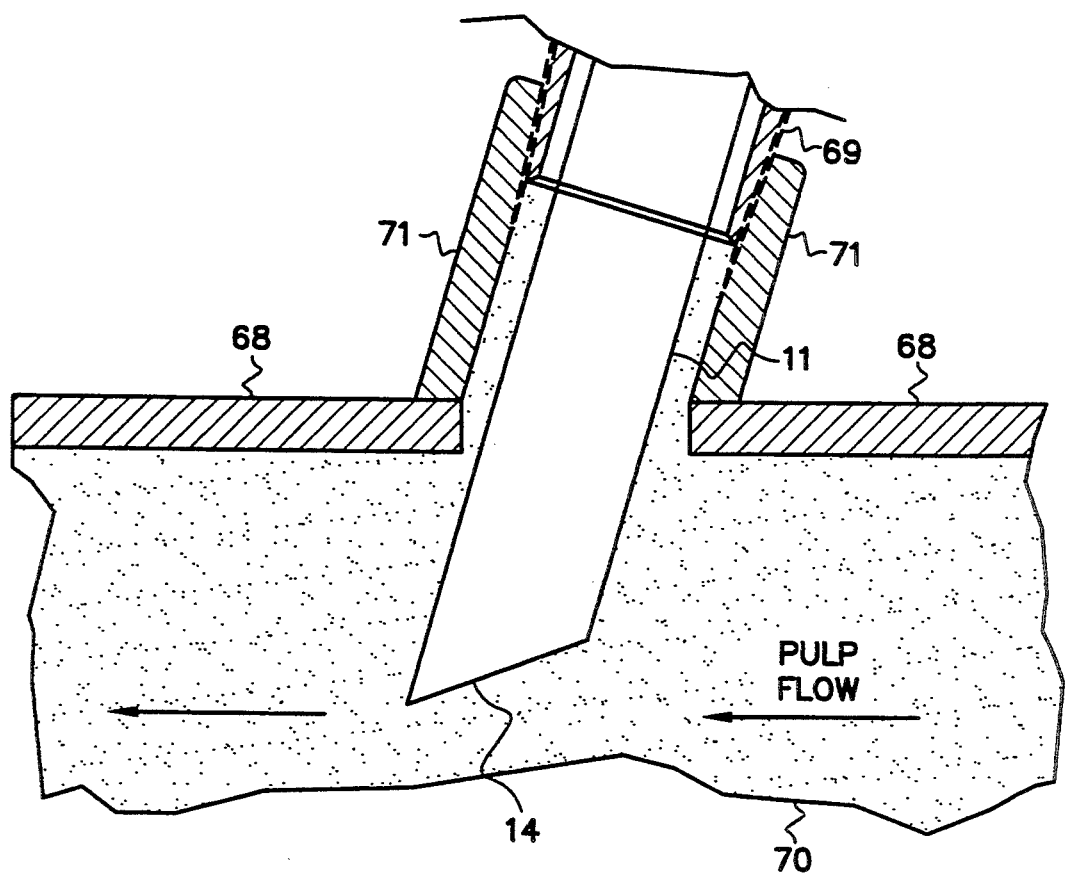
FIG. 6 is a diagram of the brightness and consistency sensor inserted in the pulp flow.

The operation of the optical sensor can be better understood by study of FIG. 6. As is shown, the optical sensor 10 is mounted on pulp container 68. In this preferred embodiment, the probe is held in threaded coupler 69 and is attached to the container 68 by mating the coupler 69 with extension 71. Depending on the condition which is being monitored, the sensor can be mounted anywhere along the production equipment where the paper is in pulp form. As is seen, the probe extends out into the pulp flow 70. Moving pulp passes around the probe and over the window 14. Light from within the probe shines through window 14 and reflects off the pulp. Light reflected back into the probe enclosure is received by fiber optic bundle 20 and transmitted to the systems electronics. The system electronics converts the fiber optic signal transmitted over the bundle into electronic signals representative of the brightness and consistency of the pulp.

Figure 7:
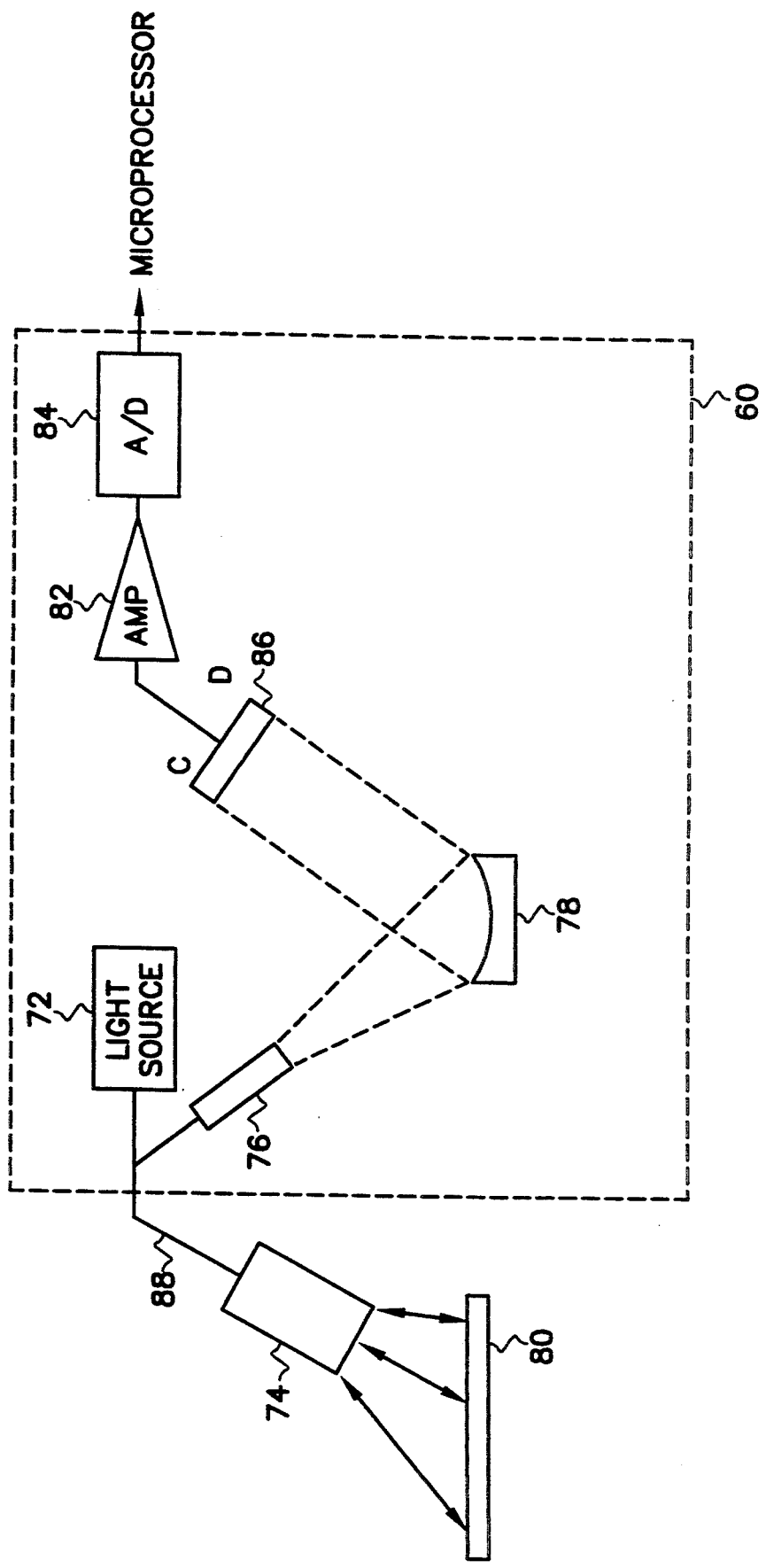
FIG. 7 is a diagram of the color sensor.

An important feature of the present invention is the intensity measurements of the reflected light made over substantially the entire visible light bandwidth region. The preferred color sensor 60 utilizes the complete visible spectrum rather than a few discreet wavelengths. The operation of the color sensor can be better understood by study of FIG. 7. In the presently preferred embodiment, light emitting/receiving end 74 performs a dual purpose of both emitting light and receiving back the reflective light. Light to be emitted is transmitted from a light source 72 through fiber optic line 88 to the light emitting/receiving end 74. Light is reflected off the object 80 and then back into the light emitting/receiving end 74. Reflected light is carried by fiber optic line 88 to disbursing element 78. On one end of fiber optic line 88 is light exiting end 76. Reflected light leaving light exiting end 76 strikes disbursing element 78. Disbursing element 78 may be a diffraction grating. The reflected light is broken into its component wavelength and reflected to detector array 86. For this embodiment, disbursing element 78 disburses and provides a flat field of focus of the spectrum (400 NM to 800 NM) on detector array 86. The focus spectrum strikes detector array 86 with 400 NM light at side C and 800 NM light at side D.

Light disbursed and reflected by disbursing element 78 is directed toward a detector array 86. Detector array 86 may be comprised of a linear sequence of N photodetectors. For this embodiment, N=128. Each photodetector is adapted to produce an electrical signal when light of a predetermined frequency impinges thereon. The magnitude of the signal is directly proportional to the intensity of the light which strikes the photodetector.

The magnitude of the signal output from the color sensor may be affected by another factor. Within the color sensor electronics controls the amount of time the photodetectors are exposed to light. The period of exposure is known as integration time. As the integration time increases, the magnitude of the signal output from the color sensor increases. When the integration time decreases, the magnitude of the signal decreases. In order to get accurate readings from the presently preferred embodiment, the integration time is held constant during operation of the color sensor.

The detector array produces an analog signal indicative of the color signature of object 80. The analog signal is amplified by amplifier 82 and then digitized by A/D converter 84, thus creating a 1×128 array of sensed component values. After digitization, the array of sensed values is transmitted to microprocessor 62.

During operation of the system, a variety of parameters may affect or influence the output of the color sensor. Four main parameters are:
reflectivity of target object
integration time of the detector array in a color sensor
ambient temperature of color sensor
color temperature and intensity of lamp Data normalization must be employed to control these parameter effects. The objective of normalization in the preferred embodiment is to determine an accurate reflectivity for spectral data of pulp using the color sensor under a variety of conditions. If the operating condition parameters were not taken into account, acquired spectra would vary so much as to not be useful in measuring pulp consistency and brightness.

In order to normalize the color sensor output, a normalization model must first be created. There are two steps in the development of a normalization model. The first step is to establish a model by testing the sensor at known reflectivity or direct light conditions. The output data, as the sensor input varies, will be predictable according to a model. Many techniques for modeling are known and may be used here.

In the second step, the now known or derived model along with the values of other parameters are used to solve for an unknown object or work piece reflectivity. The mathematical relationship for the normalization model is:

$$\text{spec}(\lambda) = f(r_t(\lambda), \tau, T_a, T_c)$$

Where:
spec $(\lambda)$=output spectrum of color sensor,
$r_t$=reflectivity of target object,
$\tau$=integration time of the detector array within the color sensor,
$T_a$=ambient temperature of color sensor,
$T_c$=color temperature and intensity of light source.

To develop the normalization equations, relationships must be established between color sensor output and influencing parameters. This is done either through experimentation or through performance information provided by the manufacturer of particular components of the sensor. For example, the Microswitch color sensor used in the presently preferred embodiment is known to respond in a linear fashion to changes in object reflectivity and detector array integration time.

According to this preferred embodiment, a linear term is added to the normalization model for the parameters of object reflectivity and integration time. The advantage of a linear model of behavior is that it can be easily updated.

Ambient temperature affects the behavior of the color sensor. The effect of these changes on the color sensor used has been determined by experiment and has been modeled by second order polynomial:

$$\text{spec}(\lambda) = c_2 T_a^2 + c_1 T_a + c_0$$

Where:
$T_a$=ambient temperature.
$c_i$=coefficients

The final parameter that affects the output of the color sensor is the color temperature and intensity of the lamp or light source within or used by the color sensor. It is known that the electrical current draw of the lamp is linearly related to its color temperature and intensity. For this reason, a current sensor is included in the color sensor we used. The output of the current sensor is used to monitor the color sensor for changes in lamp intensity. Another second order polynomial was found to approximate the lamp current over the limited range of the visible spectra. This second order polynomial is $$\text{spec}(\lambda) = d_2 C^2 + d_1 C + d_0$$

Where:
C=current of lightsource
$d_i$=coefficients

Output spectra of the color sensor were collected for different lamp color temperatures/currents by modifying the drive current of the lamp. These drive currents were used as the independent parameter in the normalization equation.

By combining the normalization equation for each of the parameters, the resulting normalization equation for the optical sensor is as follows:

$$\text{spec}(\lambda) = (a_1 r_t + a_0)(b_1 t + b_0)(c_2 T_a^2 + c_1 T_a + c_0)(d_2 C^2 + d_1 C + d_0)$$

Where:
spec $(\lambda)$=output spectrum of color sensor,
$r_t$=reflectivity of target object,
$\tau$=integration time of the detector array of the color sensor,
$T_a$=ambient temperature of color sensor,
C=current of light source.

$a_i$, $b_i$, $c_i$, $d_i$ = coefficients

In order to use the normalization equations, the coefficients need to be established through testing or other provided information. In order to provide more flexibility in modeling, the equation is multiplied out to provide 36 different coefficients.

Figure 8:
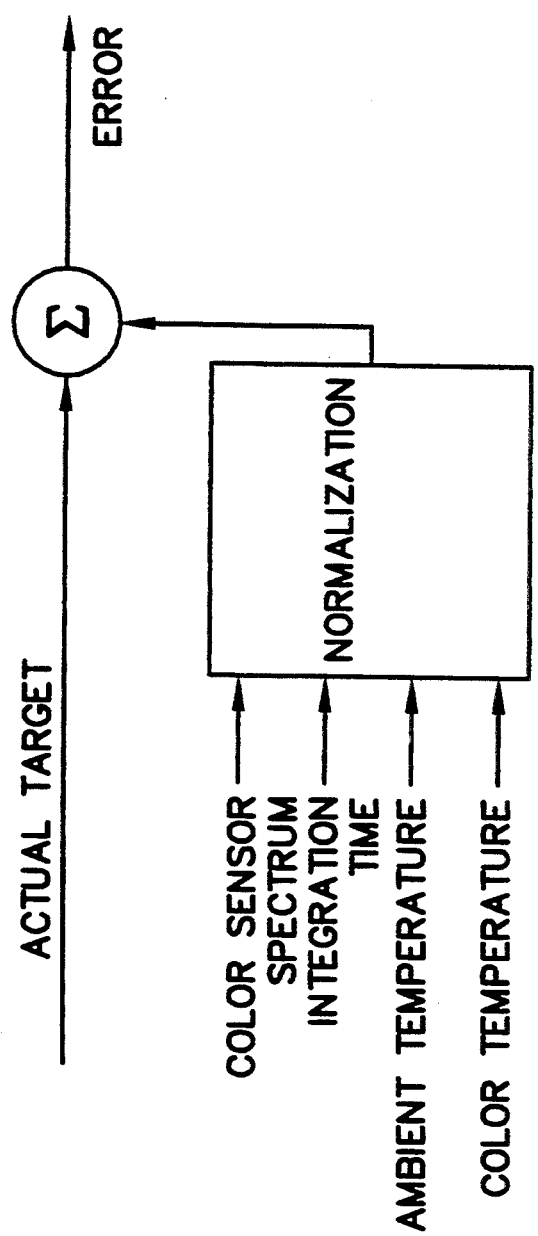
FIG. 8 is a control diagram for the normalization using just the first normalization equation.
Figure 9:
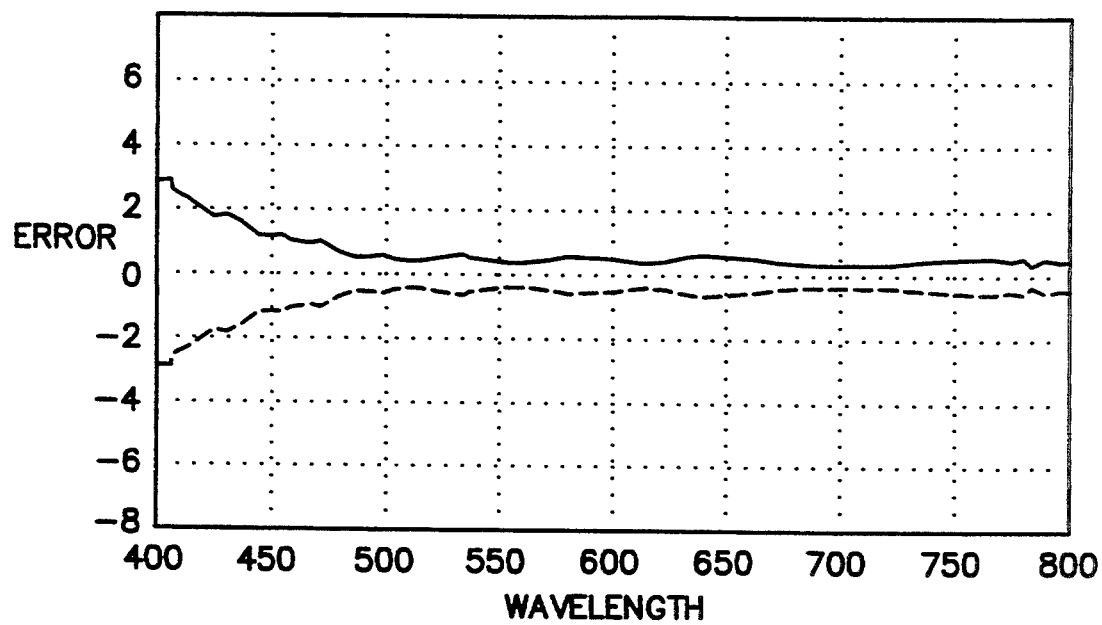
FIG. 9 is an error plot for color sensor No. 2 using normalization equation 2.
Figure 10:
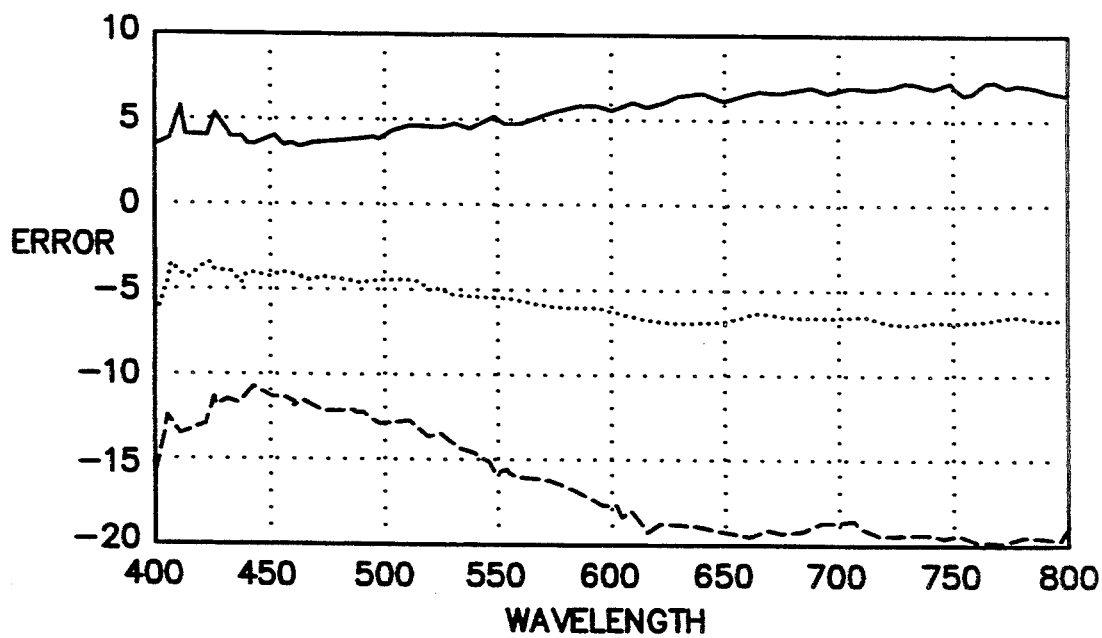
FIG. 10 is an error plot for color sensor No. 1 using normalization equation 2.

A representation of the implementation of the normalization equations is shown in the control diagram in FIG. 8. A model error is created between the normalization equation and a known target reflectivity. This model error is used to correct the coefficients of the normalization model. This technique provides compensation for the behavior of an individual color sensor. However, characterization of one color sensor will not perform well with a second color sensor. FIG. 9 shows an error plot of a second color sensor using normalization coefficients for the same sensor over the visible wavelength range. As can be seen, the error is very small. In FIG. 10, the error plot is of a first sensor using the normalization equation of the second sensor. In this case, the error is quite large. FIGS. 9 and 10 demonstrate that in order to get accurate readings, each color sensor should be characterized individually at the manufacturer of the color sensor to obtain the desired normalization performance.

A disadvantage of the normalization process described above is that each parameter can prove to be expensive and time consuming to model. Prior to installation of the sensor in the field, it must go through a testing procedure in the laboratory in order to create the normalization model. If the unit is already in the field and the normalization model needs updating, the unit must be pulled out of service and returned to the lab. In the embodiment of the invention described below, a portion of the normalization model remains constant for all units in production, and an apparatus is provided for updating the normalization model while the optical sensor is in operation.

Figure 11:
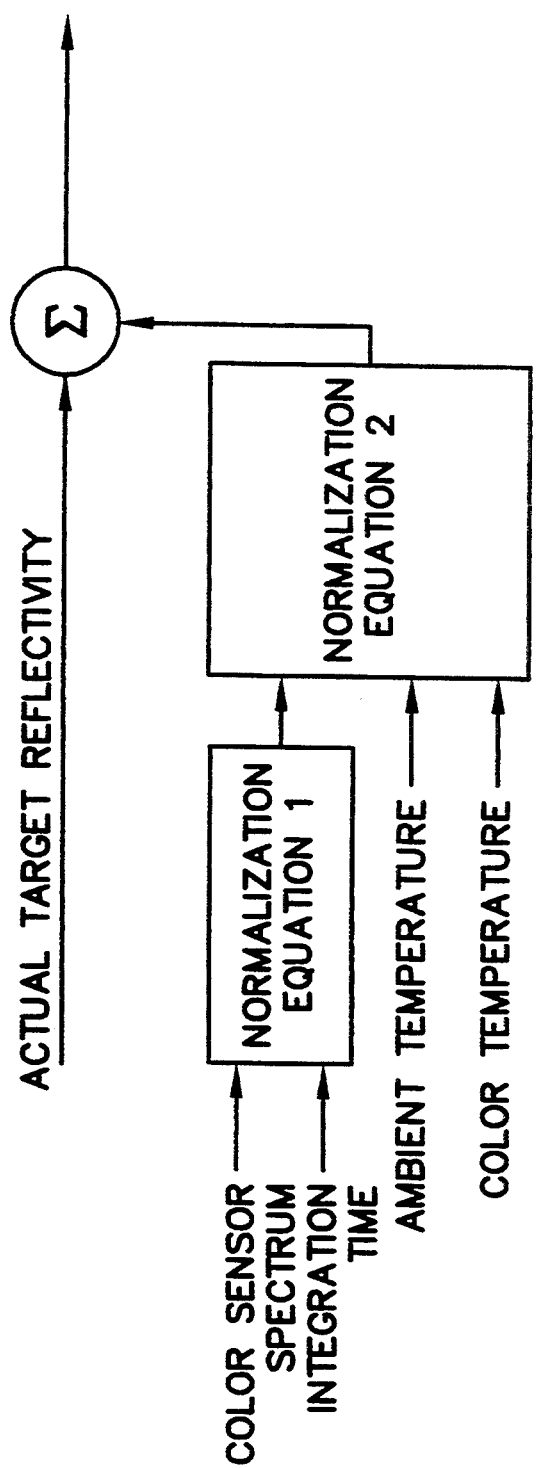
FIG. 11 is a control diagram for the normalization using both the first and second normalization equations.

The present normalization technique is depicted in the control diagram in FIG. 11. The equations depicted in the diagram are as follows:

$$\text{spec }(\lambda) = b_3 \, r_{int}(\lambda)\tau + b_2 r_{int}(\lambda)\tau + b_1 + b_0 \qquad \text{EQ.1}$$

Where:
$\tau$ = integration
spec $(\lambda)$ = output spectrum of color sensor
$r_{int}(\lambda)$ = intermediate spectral reflectivity
$b_i$ = coefficient $$r_{int}(\lambda) = (c_2 T_a^2 + c_1 T_a + c_0)(d_2 C^2 + d_1 C + d_0)(e_1 r(\lambda) + e_0) \qquad \text{EQ.2}$$

Where:
$r_{int}(\lambda)$ = intermediate spectral reflectivity
$r(\lambda)$ = spectral reflectivity of target object
$T_a$ = ambient temperature of color sensor
$C$ = current of light source
$c_i$, $d_i$, $e_i$ = coefficients In this technique, normalization equation 2 remains fixed for all time and all sensors. The coefficients in normalization equation 1 are adjusted to compensate for any differences between devices.

The input parameter variations required to determine model coefficients for normalization equation 1 are easy to obtain during manufacture and in the field. In contrast, the input parameter variation required to determine model coefficients for normalization equation 2 are expensive and time consuming to obtain. Therefore, the coefficients of normalization equation 2 will remain fixed. This equation can work because the principal difference between the output of two sensors without normalization models is an amplitude shift in the spectral intensity in response to differences in color temperature and ambient temperature. This amplitude shift can be corrected by adjusting the coefficients of normalization equation 1.

In actual operation, the model shown in EQ.2 is established through testing and provided for all color sensors. The adjustable coefficients for EQ.1 are then established for each of the color sensors. Once the models are created, the model coefficients are installed as part of the optical sensor and is ready for operation in the field. Once the optical sensor begins operating, the spectral data is output from the color sensor 60 and transmitted to the microprocessor 62. Stored in the memory 63 are the models for normalization of the spectral data. Microprocessor 62 accesses these models and the data is normalized for the predicted parameters. The spectral data is then interpreted as pulp consistency and brightness by other components of the optical sensor.

From time to time, normalization equation 1 can be updated while the sensor is out in the field. As the optical sensor operates, the performance of the system may change in ways not predicted by the models. This requires that the normalization models be periodically updated. By providing two known reflectivities, the slope and y-intersect of the linear relationship in EQ.1 can be updated.

As was described above, targets 16 and 18 have areas of known reflectivity. In order to update the normalization models in the memory 63, each target is individually rotated in front of the fiber optic bundle and multiple readings are taken for different integration times. The two reflectivities taken provide two points of spectrum output vs. reflectivity. From the measured data, a linear relationship is then established and the normalization model is updated. Once the readings are taken, the targets are rotated back to a position where they do not interfere with light reflected from the pulp. One advantage of the present invention is that the consistency and brightness sensor does not have to be removed from service in order to update the normalization model. While the probe is still immersed in the pulp, the solenoids 40 and 46 are electrically actuated and they provide torque to rotate targets 16 and 18. The targets may also be manually actuated. Because all the mechanical systems are contained within the probe enclosure, there is no possibility that the pulp flow will cause any degradation of the system.

Figure 12:
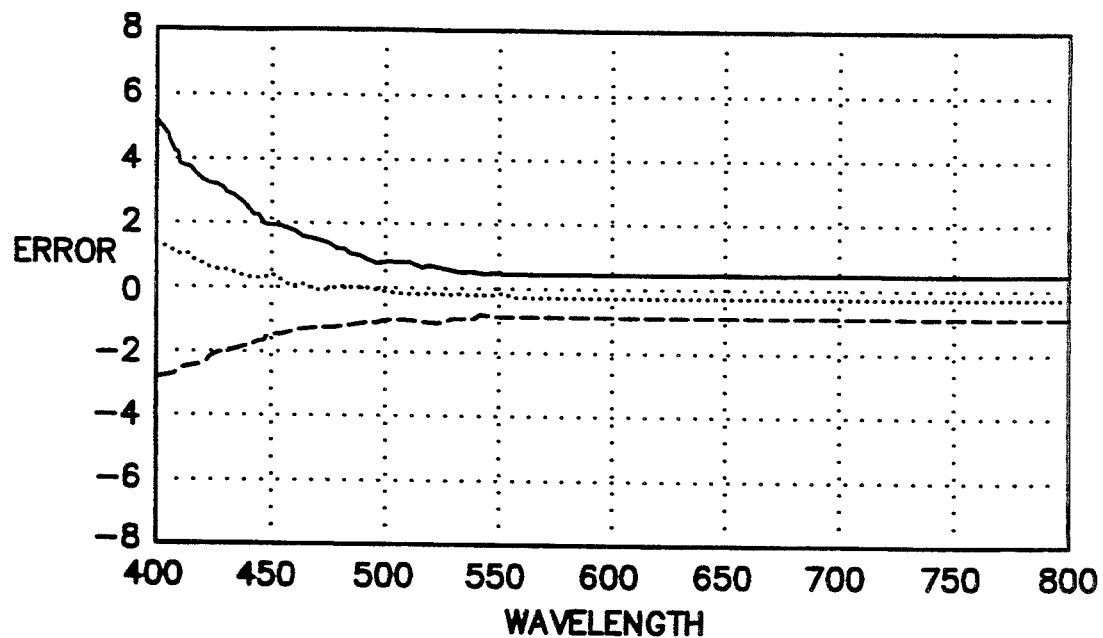
FIG. 12 is an error plot for color sensor No. 1 using normalization technique No. 2.
Figure 13:
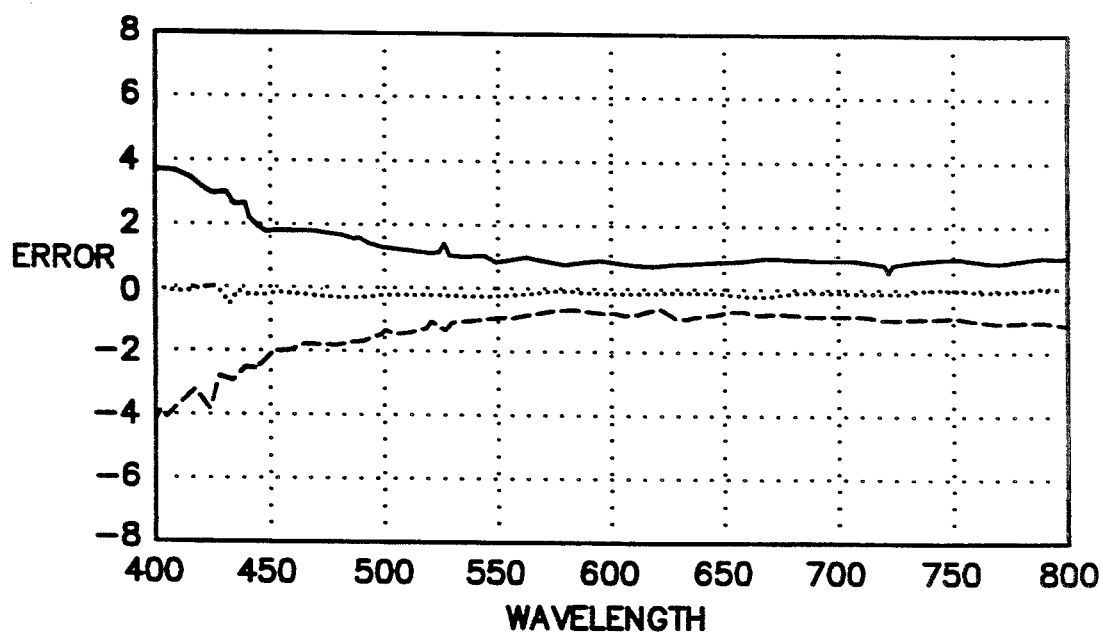
FIG. 13 is an error plot for color sensor No. 2 using normalization technique No. 2.

FIGS. 12 and 13 are error plots for two different sensors which use EQ. 1 and EQ. 2 as normalization models. Sensor no. 1 is shown in FIG. 12 while sensor no. 2 is shown in FIG. 13. For each sensor, EQ. 2 is held constant while EQ. 1 is updated using the reflective targets. As can be seen the error in both plots is minimal, especially compared to the error shown in FIG. 10.

Once the reflected light has been converted to a normalized array of sensed values, the microprocessor then converts the array into values for brightness and consistency. This is done by programming into the memory mathematical models which the microprocessor uses to interpret color sensor output. A model is created by using known mathematical relationships, developed through experimentation and regression analysis. A prerequisite of the model is that it is able to convert all 128 values stored in the array of sensed values into separate measurements for brightness and consistency. The following are an assortment of models which were found to work with the broadband color sensor for calculating brightness and consistency.

Figure 14:
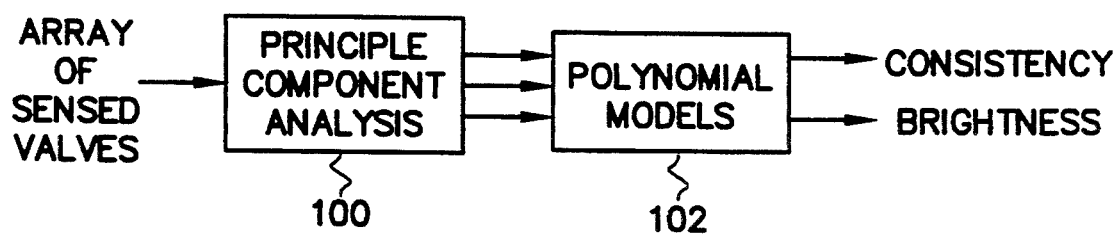
FIG. 14 is a block diagram for the linear model using principal component analysis.

One model is a polynomial model. A block diagram incorporating this model is shown in FIG. 14. In this case, two models 102 are developed, one for brightness and one for consistency. These models 102 estimate consistency and/or brightness directly as a function of the features extracted from the array of sensed values. The polynomial models can be described by the following equations:

$$\text{Con} = \alpha_1 + \alpha_2 k_1 + \alpha_3 k_2 + \alpha_4 k_3 + \alpha_5 k_1 k_2 + \alpha_6 k_1 k_3 + \alpha_7 k_2 k_3 + \alpha_8 k_1^2 + \alpha_9 k_2^2 + \alpha_{10} k_3^2 + \alpha_{11} k_1^2 k_2 + \alpha_{12} k_1^2 k_3 + \alpha_{13} k_2^2 k_1 + \alpha_{14} k_2^2 k_3 + \alpha_{15} k_3^2 k_1 + \alpha_{16} k_3^2 k_2 + \alpha_{17} k_1 k_2 k_3$$

$$\text{Bri} = \beta_1 + \beta_2 k_1 + \beta_3 k_2 + \beta_4 k_3 + \beta_5 k_1 k_2 + \beta_6 k_1 k_3 + \beta_7 k_2 k_3 + \beta_8 k_1^2 + \beta_9 k_2^2 + \beta_{10} k_3^2 + \beta_{11} k_1^2 k_2 + \beta_{12} k_1^2 k_3 + \beta_{13} k_2^2 k_1 + \beta_{14} k_2^2 k_3 + \beta_{15} k_3^2 k_1 + \beta_{16} k_3^2 k_2 + \beta_{17} k_1 k_2 k_3$$

where:
Con = consistency
Bri = pulp brightness
$k_1$, $k_2$, $k_3$ are a selection of the principle component analysis features
$\alpha_i$, $\beta_i$ = coefficients Features $k_1$, $k_2$, and $k_3$ are determined through use of principle component analysis 100. Through experimentation, a data reduction rate is chosen that maximizes the dimensional reduction of the model while minimizing the loss of information. The resulting transformation reduces the 1-by-128 sense component array to a 1-by-3 feature vector. Values for $k_1$, $k_2$ and $k_3$ are the result of the principle component analysis 100. The values are inserted in the polynomial models 102 to determine values for brightness and consistency. The coefficients ($\alpha$'s and $\beta$'s) are determined using regression analysis during experimentation.

Figure 15:
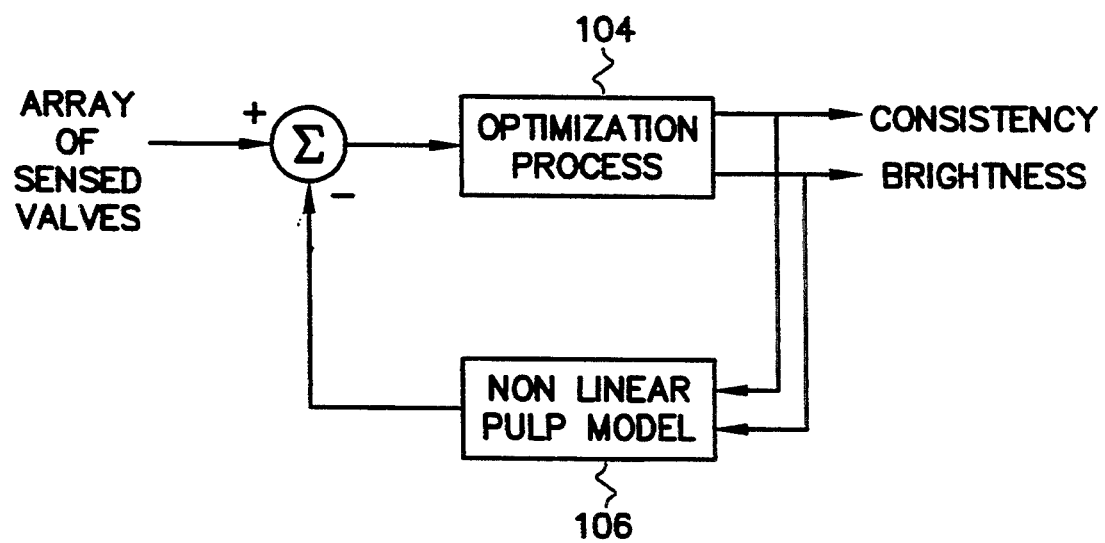
FIG. 15 is a block diagram for the optimization procedure.

Another model uses two basic pieces of physical knowledge. The first is that consistency behaves as an exponential. More specifically, its behavior is described by Beer's and Borguer's Laws. These optics laws describe the level of light transmission in a solution as a function of concentration of dye and distance. The second piece of physical knowledge is that brightness is measured using a linear scale from pulp samples that have a consistency of 100%. The values for brightness and consistency can be found from the following equation:

$$\text{ref}(\lambda) = a_1(\lambda) + a_2(\lambda).\text{Bri} + a_3(\lambda).\exp^{-\gamma(\lambda).\text{Con}} + a_4(\lambda).\text{Bri}.\exp^{-\gamma(\lambda).\text{con}}$$

where:
ref($\lambda$) = spectral reflectivity
Bri = pulp brightness
Con - pulp consistency
$a_i(\lambda)$ = coefficients As was mentioned above, this equation is linear with respect to brightness and exponential with respect to consistency. Due to the non-linear coefficients of this equation, it cannot be easily solved for brightness or consistency. As shown in the control diagram in FIG. 15, a process of numerical optimization 104 is performed whereby different values of brightness and consistency are tried in the non-linear pulp model 106 until the calculated spectral reflectivity closely matches the actual pulp spectral reflectivity. The coefficients $a(\lambda)$ and $\gamma(\lambda)$ are calculated through non-linear regression analysis.

Because the color sensor uses the whole spectrum of visible light, the non-linear model described above must be solved for every value in the array of sensed component values. Once this has been done, a best fit is made for the values of brightness and consistency. One drawback of the non-linear model is the possibility that a local error minimum (sub optimum solution) could possibly be found instead of the correct result. Another drawback is that if there is a large range of values, this iterative method is very time consuming. If the consistency and brightness range of the pulp is limited, the non-linear model is sufficient. However, if there are large ranges in the sensed values, the technique described below is more appropriate.

Still another method of providing consistency and brightness values is to use a neural network to perform the function of the model. Neural networks are generally constructed from two elements: processing units and (directed) connections between units. Each connection has a real-valued weight associated with it that indicates how strongly the source unit of the connection affects the value of the destination unit. The unit output of digital neural networks is a scalar quantity (a real number), usually some monotonic but non-linear function of the weighted sum of its input. In order for a neural network to operate, it must first be taught some sort of functionality through a training set which consists of inputs and corresponding desired outputs. This is usually in the form of a learning algorithm which is typically iterative. The algorithm requires that a set of data already be acquired in order to coordinate a training set. The most popular algorithm type for such training is known as "backpropagation". In this application, backpropagation adjusts network weights to accomplish an approximate gradient-descent minimization of a square-error criterion over the training set.

Figure 16:
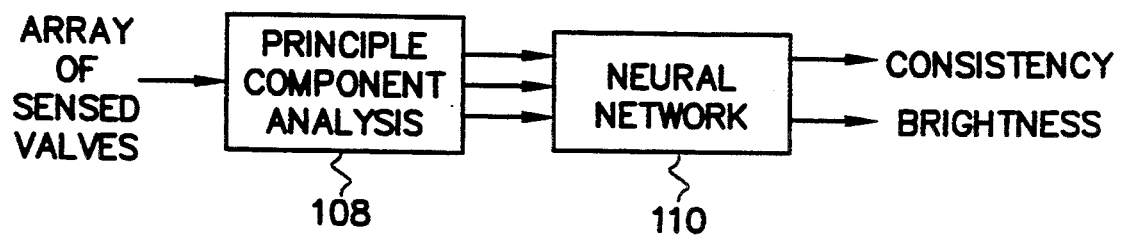
FIG. 16 is a block diagram of the neural network model using principle component analysis.
Figure 17:
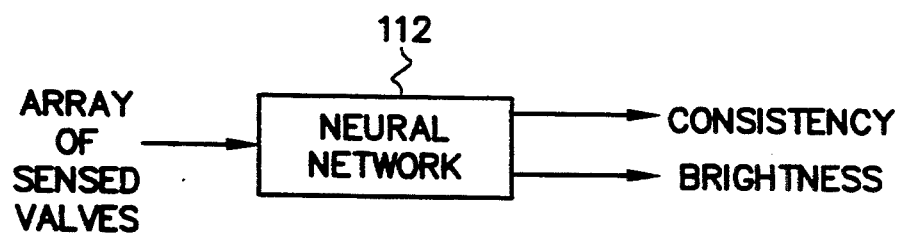
FIG. 17 is a block diagram of just the neural network model.

A variety of options exists for the use of the neural network. As shown in FIG. 16, the neural network 110 can be used in conjunction with principle component analysis 108. This will create a neural network with three inputs and either one or two outputs. The array of sensed values is run through principle component analysis 108 and then inserted in the neural network 110 to generate values for brightness and consistency. A network can also be created which uses the entire array of sensed values. To use this network in the invention there are 128 inputs and two outputs. A block diagram showing this is seen in FIG. 17. The whole array is put in the neural network 112 to calculate values for consistency and brightness.

Figure 18:
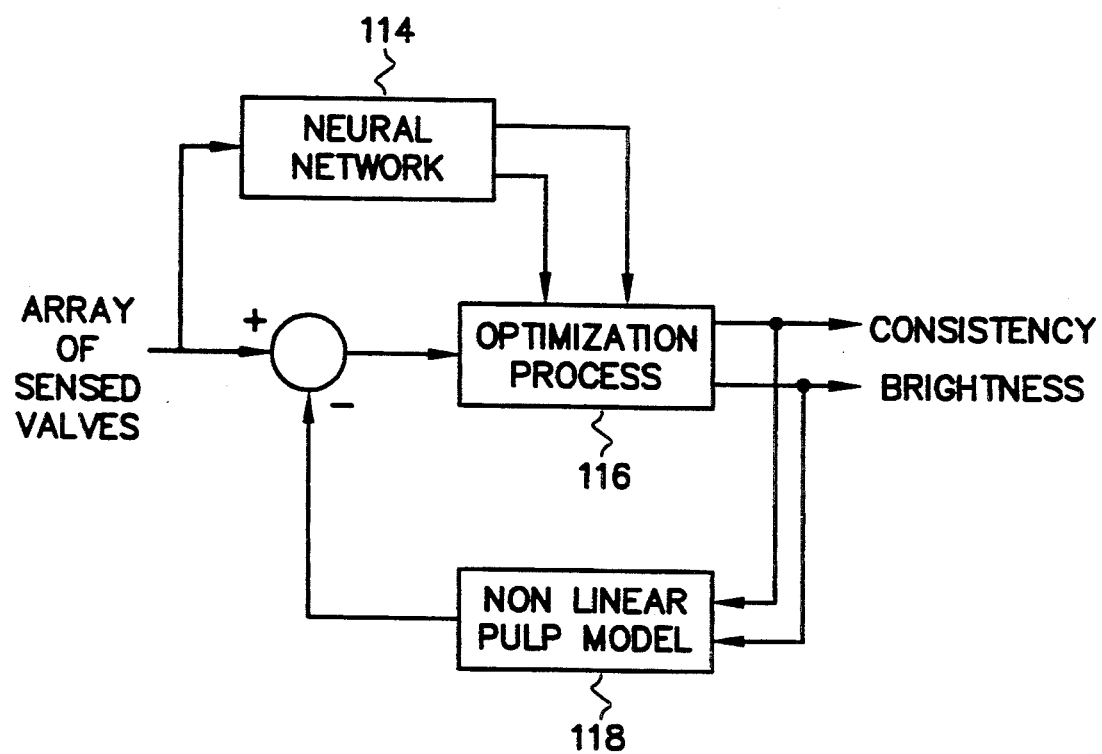
FIG. 18 is a block diagram of a combination of a neural network model and an optimization procedure.

Still another way a neural network can be used is in connection with the non-linear model described above. In the non-linear pulp model, a recursive numerical optimization technique was used to determine the consistency and brightness from the array of sensed component values. A neural network can be taught to output the same result in the numerical optimization procedure. This is a single step way to develop solutions to non-linear equations that would otherwise need iterative techniques. Depending on the size of the neural network needed for this task, the number of computations and the time needed to find a solution may also be reduced. Alternatively, as shown in FIG. 18, the output of the neural network model 114 may be used as the initial starting point for the optimization process 116 for non-linear pulp models 118. The neural network 114 generates values for consistency and brightness which are close to optimal, and then the optimization process 116 is used with the non-linear pulp model 118 to calculate the final solutions. This significantly reduces the number of search steps and time needed to find the solution. This method also saves computation time once the time has been spent training the network.

Because of the many possible applications of neural network technology to interpreting color sensor output, there is not intention to limit the preferred embodiment of the invention to the neural networks recited above. One skilled in the art of neural networks would realize that as neural network technology evolves, its application to different areas of technology as well as the present invention, would also evolve.

All of the above models can be used with the optical sensor. Each model offers the advantage of either accuracy or simplicity. Some models will only be accurate over a particular range of actual consistencies and brightnesses, while others will require more time to perform complex calculations to determine a solution. The model used depends on the circumstances.

The foregoing has been a description of a novel and non-obvious method for determining brightness and consistency for paper pulp. The inventors do not intend to be limited to only the embodiment shown and described in the application. Instead, the scope of the applicants' invention can be determined by the following claims.

We claim:

1. A method of interpreting spectral data in an optical sensor comprising the steps of:

illuminating a workpiece with a source;

receiving with a sensor means having multiple wavelength outputs light reflected from said illuminated workpiece;

generating an array of sensed values representative of the intensity of a plurality of wavelengths of light over a predetermined wavelength range, in response to the light reflected off the workpiece;

applying a predetermined mathematical model, having included values related to the amount of electrical current consumed by the source, to the array of sensed values, relating magnitudes of the array of sensed values to characteristics of the workpiece; and generating at least one output signal proportional to the characteristics of the workpiece; wherein a representation of the mathematical model is trained into a neural network which generates the output signals.

2. A method of interpreting spectral data in an optical sensor comprising the steps of:

illuminating a workpiece with a source;

receiving with a sensor means having multiple wavelength outputs light reflected from said illuminated workpiece;

generating an array of sensed values representative of the intensity of a plurality of wavelengths of light over a predetermined wavelength range, in response to the light reflected off the workpiece;

applying a predetermined mathematical model, having included values related to the amount of electrical current consumed by the source, to the array of sensed values, relating magnitudes of the array of sensed values to characteristics of the workpiece; and generating at least one output signal proportional to the characteristics of the workpiece wherein the workpiece is paper pulp and the characteristics are brightness and consistency.

3. The method of interpreting spectral data in an optical sensor of claim 2 wherein brightness of the paper pulp is determined by the linear model:

$$\beta_1 + \beta_2 k_1 + \beta_3 k_2 + \beta_4 k_3 + \beta_5 k_1 k_2 + \beta_6 k_1 k_2 + \beta_7 k_2 k_3 + \beta_8 k_1^2 + \beta_9 k_2^2 + \beta_{10} k_3^2 + \beta_{11} k_1^2 k_2 + \beta_{12} k_1^2 k_3 + \beta_{13} k_2^2 k_1 + \beta_{14} k_2^2 k_3 + \beta_{15} k_3^2 k_1 + \beta_{16} k_3^2 k_2 + \beta_{17} k_1 k_2 k_3$$

where $k_1$, $k_2$, $k_3$ are selected principle component features of the array of sensed values.

4. The method of interpreting spectral data in an optical sensor of claim 2 wherein consistency of the paper pulp is determined by the linear model:

$$\alpha_1 + \alpha_2 k_1 + \alpha_3 k_2 + \alpha_4 k_3 + \alpha_5 k_1 k_2 + \alpha_6 k_1 k_3 + \alpha_7 k_2 k_3 + \alpha_8 k_1^2 + \alpha_9 k_2^2 + \alpha_{10} k_3^2 + \alpha_{11} k_1^2 k_2 + \alpha_{12} k_1^2 k_3 + \alpha_{13} k_2^2 k_1 + \alpha_{14} k_2^2 k_3 + \alpha_{15} k_3^2 k_1 + \alpha_{16} k_3^2 k_2 + \alpha_{17} k_1 k_2 k_3$$

where $k_1$, $k_2$, $k_3$ are selected principle component features of the array of sensed values.

5. The method of interpreting spectral data in an optical sensor of claim 2 wherein the brightness and consistency of the paper pulp are determined by the non-linear model:

$$\text{ref}(\lambda) = a_1(\lambda) + a_2(\lambda).\text{Bri} + a_3(\lambda).\exp^{-\gamma(\lambda).Con} + a_4(\lambda).\text{Bri}.\exp^{-\gamma(\lambda).con}$$

where Bri is brightness, Con is consistency, ref ($\lambda$) is the intensity of one wavelength of light in the array of sensed values and the non-linear model is solved for the wavelengths in the array of sensed values.

6. The method of interpreting spectral data in an optical sensor of claim 2 wherein a neural network calculates values of brightness and consistency for wood pulp.

7. The method of interpreting spectral data in an optical sensor of claim 6 wherein the neural network is trained to receive the selected principal component features of the array of sensed values and output values for the brightness and consistency of the wood pulp.

8. The method of interpreting spectral data in an optical sensor of claim 6 wherein the neural network is trained to receive all the wavelengths in the array of sensed values and output values for brightness and consistency.

9. The method of interpreting spectral data in an optical sensor of claim 6 wherein the neural network is combined with the non-linear model to calculate the brightness and consistency of the wood pulp.

* * * * *